United States Patent
Gallant et al.

[11] Patent Number: 6,149,128
[45] Date of Patent: Nov. 21, 2000

[54] KEYED CAP FOR GAS OUTLET VALVE

[75] Inventors: Dennis J. Gallant, Harrison, Ohio; Michael Buccieri, Greenfield, Ind.; Edward W. Catton, New Palestine, Ind.; Teddy L. Johnson, Batesville, Ind.; John D. Vogel, Columbus, Ind.; James N. Grote, Batesville, Ind.; Douglas C. Ambach, Hamilton, Ohio; Gary L. Najmon; Nicholas C. Batta, both of Batesville, Ind.; Thomas J. Slanker, Cincinnati, Ohio; Dale A. Nobbe, Oldenburg, Ind.; Richard E. Hoffman, Overland Park, Kans.; Kenneth M. Merkel, Greensburg, Ind.; Donald L. Mobley, Batesville, Ind.; Chris L. Hildenbrand, Greensburg, Ind.; Scott McCormick, Cincinnati, Ohio

[73] Assignee: Hill-Rom, Inc., Batesville, Ind.

[21] Appl. No.: 09/164,291

[22] Filed: Oct. 1, 1998

Related U.S. Application Data

[60] Provisional application No. 60/060,663, Oct. 2, 1997, and provisional application No. 60/060,943, Oct. 3, 1997.

[51] Int. Cl.[7] .............................. F16K 51/00; F16K 35/00
[52] U.S. Cl. ............................................................. 251/149
[58] Field of Search ................................. 251/149.4, 149, 251/149.6, 149.1; 604/905

[56] References Cited

U.S. PATENT DOCUMENTS

| | | |
|---|---|---|
| 3,004,777 | 10/1961 | Buonaccorsi. |
| 3,448,760 | 6/1969 | Cranage ................... 251/149.6 |
| 3,544,257 | 12/1970 | Cranage ................... 251/149.6 |
| 3,643,985 | 2/1972 | Cranage ...................... 285/189 |
| 4,613,112 | 9/1986 | Phlipot et al. ........... 251/149.6 |
| 4,619,640 | 10/1986 | Potolsky et al.. |
| 4,696,326 | 9/1987 | Sturgis ..................... 251/149.6 |
| 4,718,699 | 1/1988 | Kulish et al.. |
| 5,197,511 | 3/1993 | Kohn et al. .............. 251/149.6 |
| 5,725,511 | 3/1998 | Urrutia ........................ 604/905 |

FOREIGN PATENT DOCUMENTS

| | | |
|---|---|---|
| 2406776 | 5/1979 | France. |
| 2625545 | 7/1989 | France. |
| 2642139 | 7/1990 | France. |

*Primary Examiner*—Kevin Shaver
*Assistant Examiner*—Eric Keasel
*Attorney, Agent, or Firm*—Barnes & Thornburg

[57] ABSTRACT

A gas valve apparatus is configured to receive a gas specific adapter. The apparatus includes a gas valve body having a first keying mechanism, and a cap coupled to the gas valve body. The cap includes a keyed front face having a gas outlet configured to receive the gas specific adapter. The cap also includes a second keying mechanism configured to mate with the first keying mechanism on the gas valve body to permit the cap to be coupled to the valve body.

20 Claims, 10 Drawing Sheets

FIG. 13 OXYGEN
FIG. 14 AIR
FIG. 15 VAC

KEYED CAP FOR GAS OUTLET VALVE

This application claims the benefit of U.S. provisional application Ser. No. 60/060,663 filed Oct. 2, 1997 and U.S. provisional application Ser. No. 60/060,943 filed Oct. 3, 1997.

The present invention relates to an improved cap apparatus for a gas outlet valve. More particularly, the present invention relates to a cap which can be keyed to a plurality of different specific gas outlets to ensure that a proper cap is installed on a particular gas specific gas outlet valve.

It is known to provide gas outlet valves coupled to movable gas blocks within head walls of hospital rooms or other locations to supply gases to a room. More specifically, gas valves may be connected to a hose in an O/R column, or to a hose barb and hose suspended from a ceiling as a pendant. Seven gas outlets are typically made available including oxygen, air, nitrous oxide, nitrogen, carbon dioxide, helium, and vacuum. Typically, gases are supplied to the hospital room through a gas manifold. Gas outlet blocks are connected to the manifold by hoses. Gas outlet valves have gas specific threads for coupling the valves to the outlet blocks. The conventional gas outlet valves include a valve body having a check valve, an internal spring, and poppet valve. A cap is coupled to the valve body. The cap has a clock face which is keyed to be gas specific for adapters that are connected to the clock face of the cap.

After a predetermined amount of use, the gas outlet valves must be serviced. Particularly, the valves are removed to replace O-ring seals within the valve. In order to gain access to the inside of the valve, the caps are removed. A problem associated with conventional gas outlet valves and caps is that the caps may be inadvertently installed onto the wrong gas outlet valve after servicing.

The present invention provides a gas specific, keyed cap which is only able to be coupled to a matching gas outlet valve. This keyed cap of the present invention reduces the likelihood that the wrong gas cap will be installed on a specific gas outlet valve.

According to one aspect of the present invention, a gas valve apparatus is configured to receive a gas specific adapter. The apparatus includes a gas valve body having a first keying mechanism, and a cap coupled to the gas valve body. The cap includes a keyed front face having a gas outlet configured to receive the gas specific adapter. The cap also includes a second keying mechanism configured to mate with the first keying mechanism on the gas valve body to permit the cap to be coupled to the valve body.

In one illustrated embodiment, the gas valve body includes a keying ring formed to include spaced apart slots, and the cap includes a flange formed to include spaced apart tabs configured to enter the spaced apart slots to permit the cap to be coupled to the gas valve body. Illustratively, the keying ring is a separate ring coupled to the gas valve body. Also illustratively, a set screw is coupled to the gas valve body. The set screw provides a stop to position the separate ring on the gas valve body.

In another illustrated embodiment, a separate sleeve is formed to include the spaced apart slots. The sleeve is coupled to the gas valve body. Illustratively, the cap includes a collar formed to include the spaced apart tabs.

In yet another illustrated embodiment, the front face of the cap includes keys spaced apart by a predetermined angle which are configured to mate with keys on the gas specific adapter. The spaced apart slots formed in the ring of the gas valve body and the spaced apart tabs formed on the cap also being spaced apart at the predetermined angle.

In still another illustrated embodiment, the gas valve body is formed to include spaced apart tabs, and the cap is formed to include spaced apart slots configured to receive the spaced apart tabs of the gas valve body to permit the cap to be coupled to the gas valve body. Illustratively, the tabs are formed on a separate sleeve coupled to the gas valve body.

In a further illustrated embodiment, a ring is configured to be coupled to the valve body. The ring includes radially inwardly extending key portions. The cap is formed to include spaced apart slots configured to receive the key portions of the ring to permit the cap to be coupled to the gas valve body.

In another illustrated embodiment, a sleeve is coupled to the gas valve body. The sleeve is formed to include an annular groove having a predetermined diameter. The cap includes an annular flange having the same predetermined diameter as the annular groove to permit the flange to mate with the groove formed in the sleeve. Illustratively, the sleeve includes an inner surface formed to include a guide slot configured to slide over a set screw coupled to the gas valve body. The sleeve is also formed to include an aperture aligned with the set screw to permit the set screw to be removed through the sleeve.

In yet another illustrated embodiment, a first collar is coupled to the gas valve body. The first collar is formed to include an annular groove having a predetermined diameter. A second collar is coupled to the cap. The second collar is formed to include an annular ring having the same predetermined diameter as the diameter of the annular groove to permit the cap to mate with the gas valve body.

In still another illustrated embodiment, a collar is coupled to the gas valve body. The collar is formed to include a ring having a predetermined diameter. The cap is formed to include an annular groove having a diameter the same as the predetermined diameter of the ring to permit the cap to be coupled to the gas valve body.

Illustratively, the gas valve body is configured to be coupled to one of a gas block, a hose in an O/R column, and a hose barb and hose suspended from a ceiling as a pendant. The gas valve body and the gas specific adapter are each configured to supply one of oxygen, air, nitrous oxide, nitrogen, carbon dioxide, helium and vacuum.

According to another aspect of the present invention, a gas valve apparatus is configured to receive a gas specific adapter. The apparatus includes a gas specific valve body, and a gas specific cap coupled to the valve body. The cap includes a keyed front face having a gas outlet configured to receive the gas specific adapter. The apparatus also includes means for keying the valve body to the cap so that only the gas specific cap is capable of being coupled to the gas specific valve body.

In an illustrated embodiment, the keying means includes spaced apart slots formed in one of the valve body and the cap, and spaced apart tabs formed on the other of the valve body and the cap. The spaced apart tabs are configured to enter the spaced apart slots to permit the cap to be coupled to the gas valve body.

In another illustrated embodiment, the keying means includes annular groove having a predetermined diameter formed in one of the valve body and the cap, and an annular ring formed on the other of the valve body and the cap. The annular ring has the same predetermined diameter as the annular groove to permit the cap to be coupled to the valve body.

Additional objects, features, and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
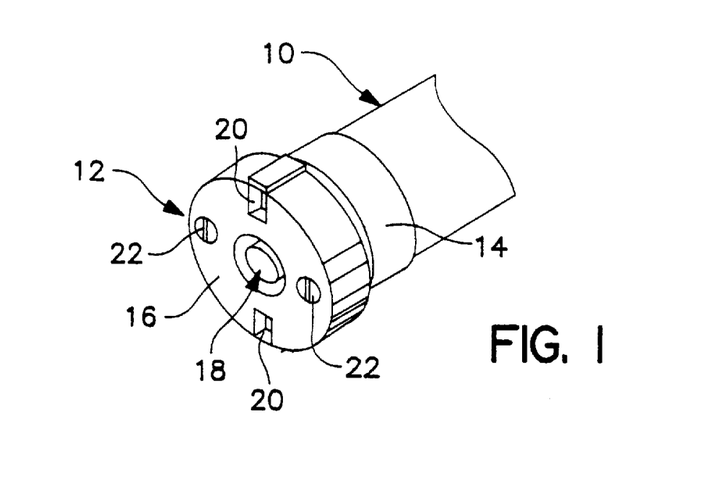
FIG. 1 is a perspective view of a conventional gas outlet valve and cap.

Referring now to the drawings, FIG. 1 illustrates a conventional gas valve including a gas valve body 10 and a cap 12 coupled to the gas valve body 10. The cap 12 includes a flange 14 and a front clock face 16. Front face 16 is formed to include a gas outlet 18, and a pair of keyed openings 20 so that an adapter coupled to the cap 12 is gas specific. A pair of screws 22 extend through the cap 12 and are coupled to a component of the valve body 10.

Figure 2:
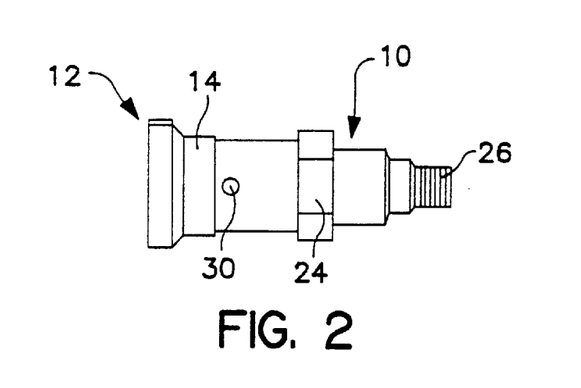
FIG. 2 is a side elevational view of the cap of FIG. 1 coupled to the valve body.
Figure 3:
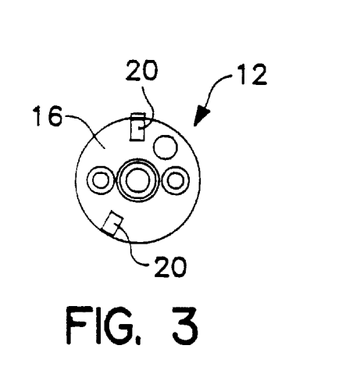
FIG. 3 is a front elevational view illustrating the outer keyed configuration of a nitrous oxide clock face on a cap.
Figure 4:
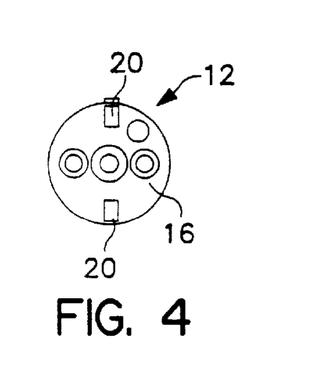
FIG. 4 is a front view illustrating an oxygen configuration of the front clock face of the cap.
Figure 5:
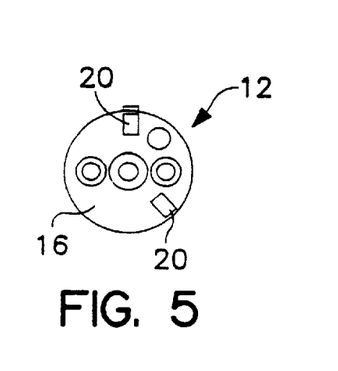
FIG. 5 is a front view illustrating an air configuration of the front clock face of the cap.
Figure 6:
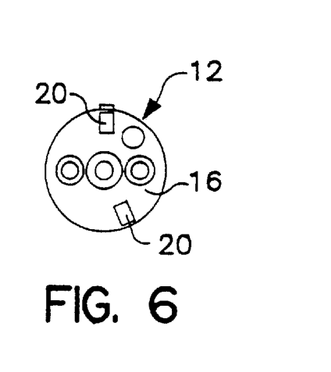
FIG. 6 is a front view illustrating a vacuum configuration of the front clock face of the cap.

As illustrated in FIG. 2, valve body 10 includes a hex nut 24 and threads 26 for coupling the valve body 10 to a gas block 28 or other connection. Although a gas block 28 is shown in the drawings, it is understood that the valve body may be coupled to any suitable gas connection such as a hose in an O/R column, or to a hose barb and hose suspended from a ceiling as a pendant. The threads 26 are ¼ inch NPT. Set screw 35 coupled to gas block 28 makes the valve body gas specific. A pair of set screws 30 extend through valve body 10 to hold internal components of the valve in place.

FIGS. 3–6 illustrate different configurations of the keyed outer clock face 16 of the cap 12. The openings 20 are formed at different locations for different types of gases. Illustratively, the gas valves may supply nitrous oxide, oxygen, air, vacuum, nitrogen, carbon dioxide, helium, or vacuum. Each of these gases has a different outer keyed configuration so that adapters (not shown) coupled to the cap 12 are gas specific.

A problem associated with conventional caps 12 is that the caps are interchangeable on to various types of valve bodies 10. In other words, when cap 12 is removed for servicing of the components of the valve 10, the cap 12 could inadvertently be placed on a gas outlet valve body 10 for the wrong type of gas. The present invention is designed to provide a keyed cap for both connection to the adapter coupled to the cap 12 and also for connection between the cap 12 and the valve body 10.

Figure 7:
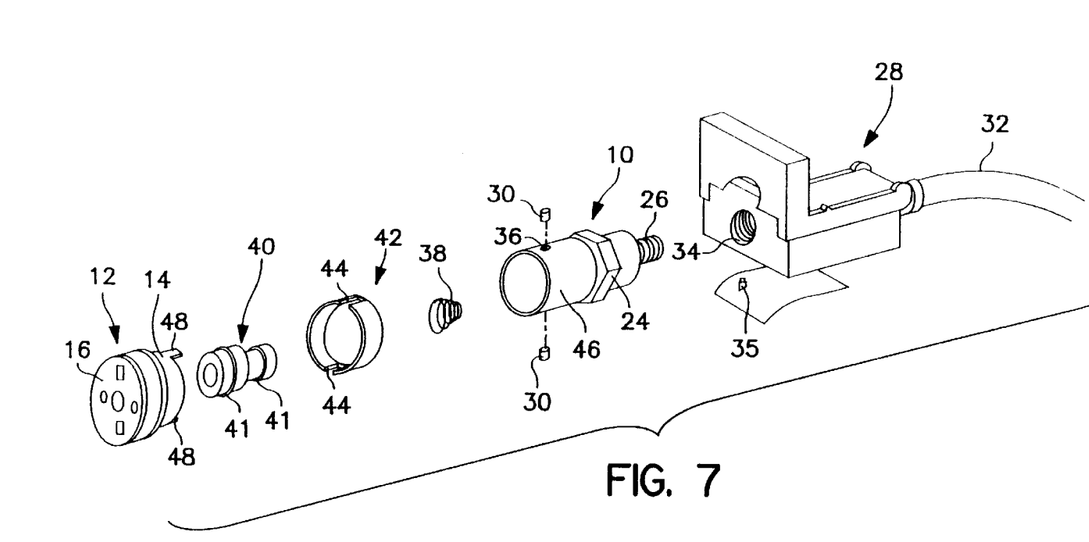
FIG. 7 is an exploded perspective view of a first embodiment of the present invention which provides a keyed cap which is configured to be coupled only to a specific matching keyed gas outlet so that a particular gas cap cannot be inadvertently connected to the wrong gas outlet valve.
Figure 8:
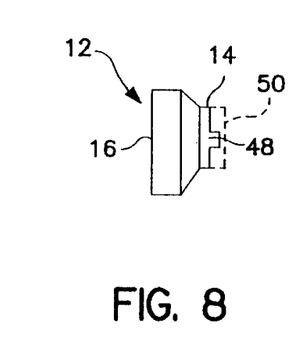
FIG. 8 illustrates a plastic machined cap configured to include projections or tabs to fit within slots formed within a ring that is coupled to the valve body to provide the keyed, gas specific cap.
Figure 9:
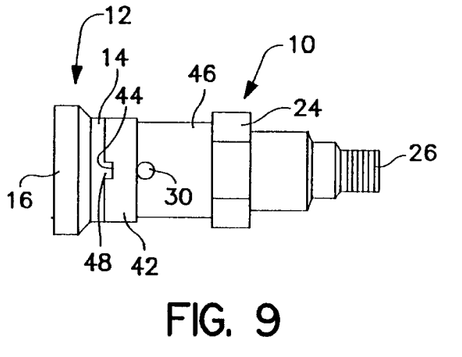
FIG. 9 is a side elevational view illustrating the machined plastic cap installed on the valve body and mated with the slotted ring which is coupled to the valve body.

A first embodiment of the present invention is illustrated in FIGS. 7–9. Gas outlet block 28 is coupled to a supply line 32. Gas block 28 includes threads 34 configured to mate with threads 26 on valve body 10. FIG. 7 illustrates that set screws 30 extend through apertures 36 formed in valve body 10. Valve components include a spring 38 and a poppet valve 40 having O-ring seals 41.

The present invention provides a keying ring 42 formed to include slots 44. Ring 42 includes an inner diameter slightly larger than the outer diameter of cylindrical portion 46 of valve body 10. The ring 42 is configured to fit over the cylindrical portion 46 of valve body 10 and is preferably glued into place to secure the ring 42 to the valve body 10.

The plastic cap 12 is machined to remove a portion of flange 14 and provide index tabs 48 aligned with slots 44 in ring 42. Ring 42 is formed with slots 44 at different orientations depending upon the particular type of gas supplied to valve body 10. These orientations may be similar to the orientations illustrated in FIGS. 3–5. The slots 44 are positioned so that only one cap 12 designed specifically for the type of gas supplied by the valve may be coupled to the valve body 10 with tabs 48 aligned with slots 44.

FIGS. 8 and 9 illustrate further details of the embodiment of FIG. 7. Specifically, FIG. 8 illustrates a portion shown by dotted lines 50 of flange 14 which is removed to form tabs 48. FIG. 9 illustrates the ring 42 and cap 12 installed on the valve body 10 with the tabs 48 located within the slots 44.

In order to retrofit an existing valve body 10 in the field, the existing cap 12 is removed. Existing set screws 30 are replaced with a longer set of set screws 30 which extend above cylindrical wall 46 to provide stops. Ring 42 is then installed over cylindrical portion 46 of valve body 10 and glued to the valve body 10. The ring 42 seats against the larger set screws 30 as shown in FIG. 9. A replacement cap 12 illustrated in FIG. 7 that has been machined to form tabs 48 is then installed. The tabs 48 and slots 44 prevent the wrong type gas cap 12 from being installed on to the valve body 10.

Figure 10:
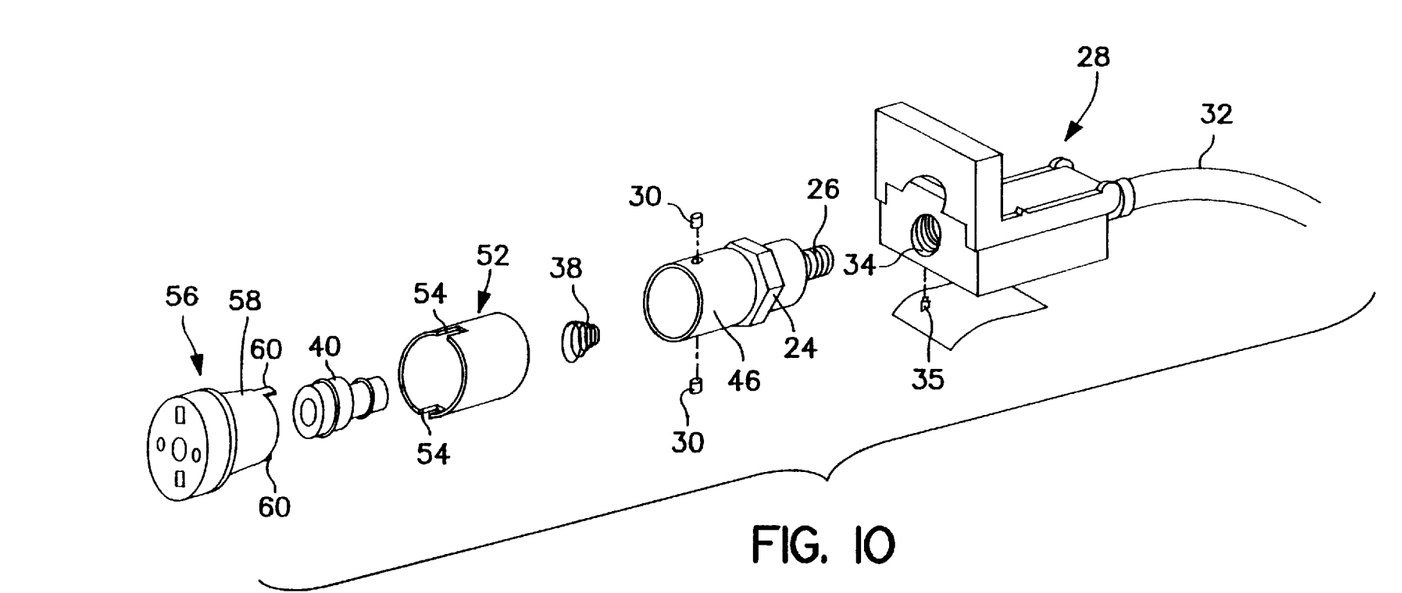
FIG. 10 is an exploded perspective view illustrating a gas valve outlet, a gas block, and a molded cap which includes an extended collar and keyed tabs configured to fit within indexed slots of a sleeve coupled to the valve body.
Figure 11:
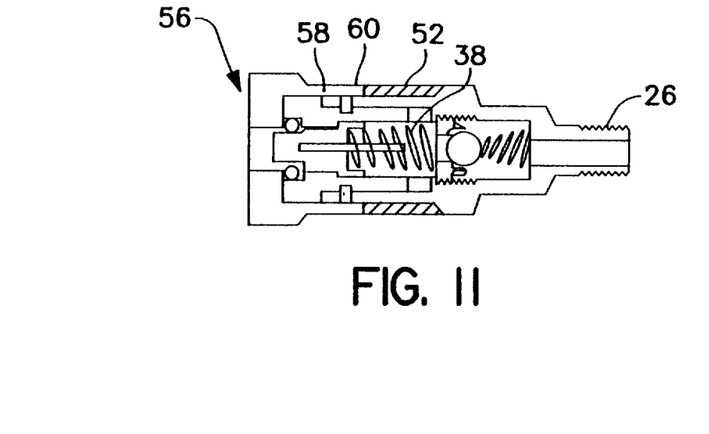
FIG. 11 is a sectional view taken through the assembly of FIG. 10 with the sleeve and cap installed on the valve body.

FIGS. 10 and 11 illustrate another embodiment of the present invention. Those numbers referenced by numbers identical to the previous figures perform the same or similar function. In the FIG. 10 embodiment, sleeve 52 is larger and includes index slots 54. Sleeve 52 is glued to valve body 10. A new molded cap 56 includes an extended collar 58 having keyed tabs 60. FIG. 11 is a sectional view illustrating the sleeve 52 and cap 56 installed on to the valve body 10. Set screws 30 are accessible by removing cap 56.

Figure 12:
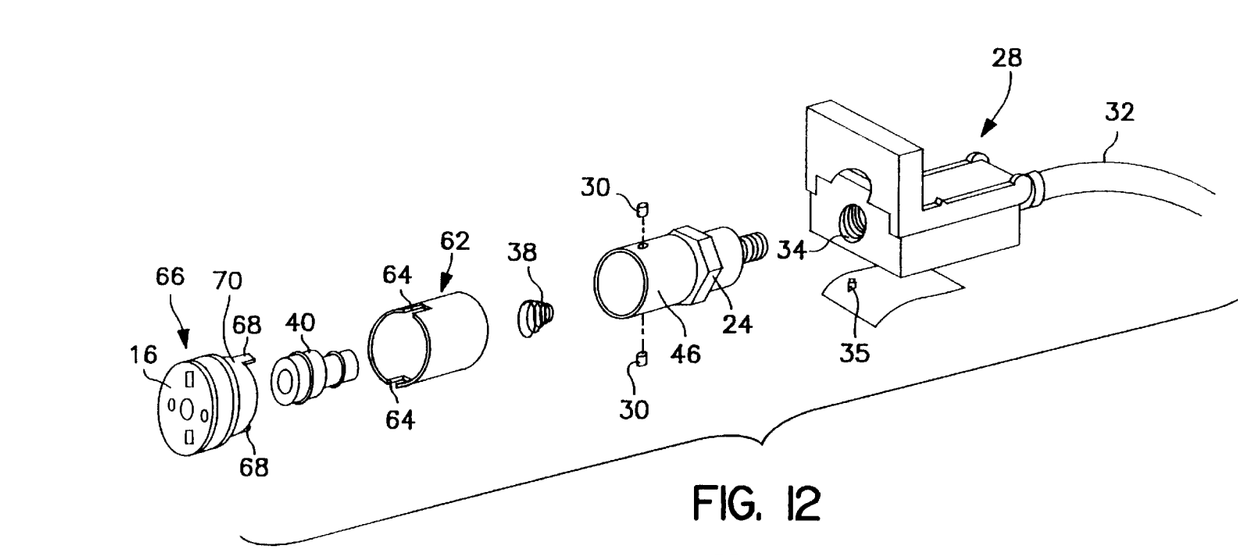
FIG. 12 is an exploded perspective view of another embodiment of the present invention including a cap with index tabs configured to mate with a sleeve having index slots for receiving the tabs.

FIG. 12 illustrates another embodiment of the present invention. Those numbers referenced by numbers in the previous embodiments perform the same or similar function. In the FIG. 12 embodiment, sleeve 62 is formed to include slots 64. Cap 66 is formed to include tabs 68 extending away from flange 70. Tabs 68 are configured to mate with slots 64 to provide a keyed cap which is gas specific. Sleeve 62 is glued or otherwise fastened to valve body 10.

Figures 13, 14, 15:
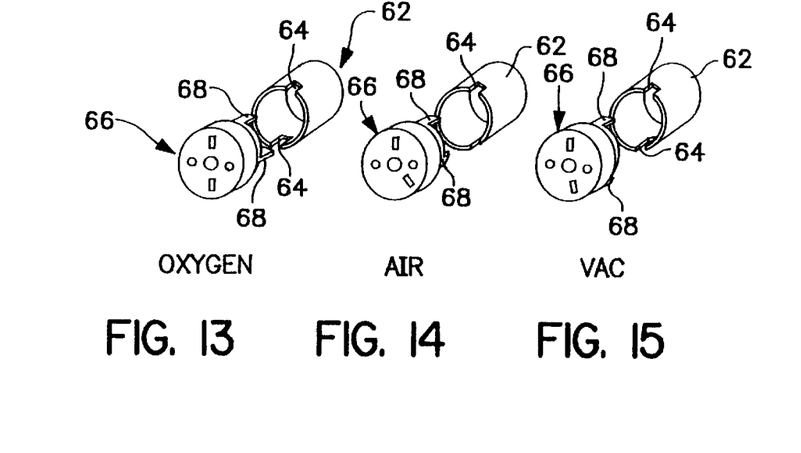
FIG. 13 is a perspective view illustrating the tab and slot orientations for an oxygen cap and sleeve.
FIG. 14 is a perspective view illustrating the tab and slot orientations for an air cap and sleeve.
FIG. 15 is a perspective view illustrating the tab and slot orientations for a vacuum cap and sleeve.

FIGS. 13–15 illustrate various gas specific caps 66 and sleeves 62 in which the slots 64 formed in sleeve 62 are aligned at different angular orientations. The tabs 68 on caps 66 are also formed at the matching angular orientations so that the caps 66 can mate only with specific sleeves 62 for the particular gas specific valve body 10.

Figures 16, 17:
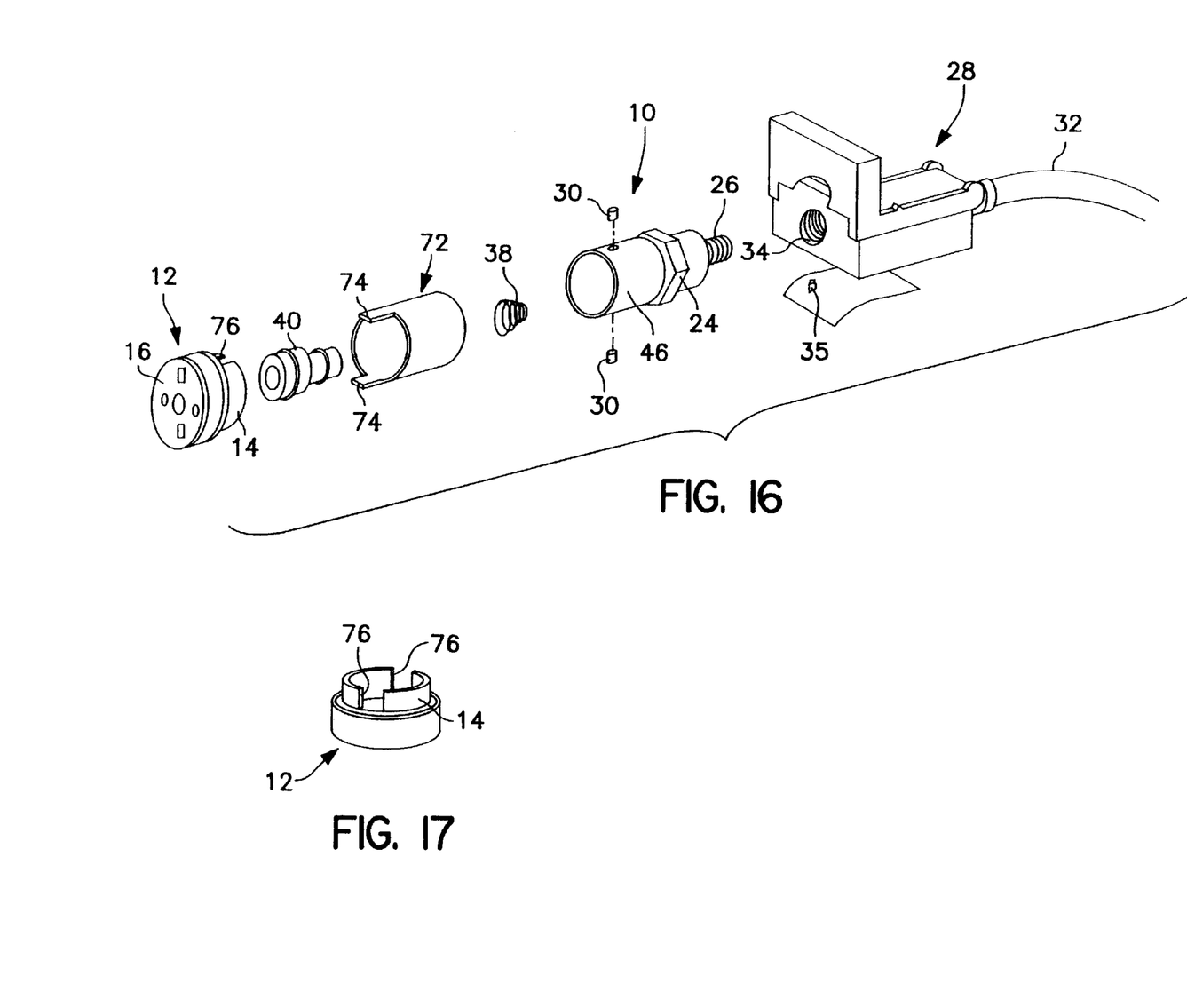
FIG. 16 is an exploded perspective view of another embodiment of the present invention in which the cap is machined to include slots and an index sleeve is formed with tabs configured to enter the slots in the cap.
FIG. 17 is a perspective view further illustrating machined slots in an existing cap.

FIG. 16 illustrates yet another embodiment of the present invention. Those numbers referenced by numbers identical to the previous figures perform the same or similar function. In the FIG. 16 embodiment, a sleeve 72 is formed to include tabs 74. Sleeve 72 is coupled to cylindrical surface 46 of valve body 10 by gluing or other suitable permanent connection. In the embodiment of FIG. 16, the flange 14 of cap 12 is machined to include keyed slots 76 aligned with tabs 74 on sleeve 72. The slots 76 formed in flange 14 are further illustrated in FIG. 17. Once the sleeve 72 is coupled to the valve body 10, only caps 12 having the appropriately spaced slots 76 are able to be coupled to the valve body 10. Again, the tabs 74 and slots 76 are spaced at different angular orientations for each of the various specific gases. This prevents the wrong cap 12 from being coupled to gas outlet body 10.

Figures 18, 19:
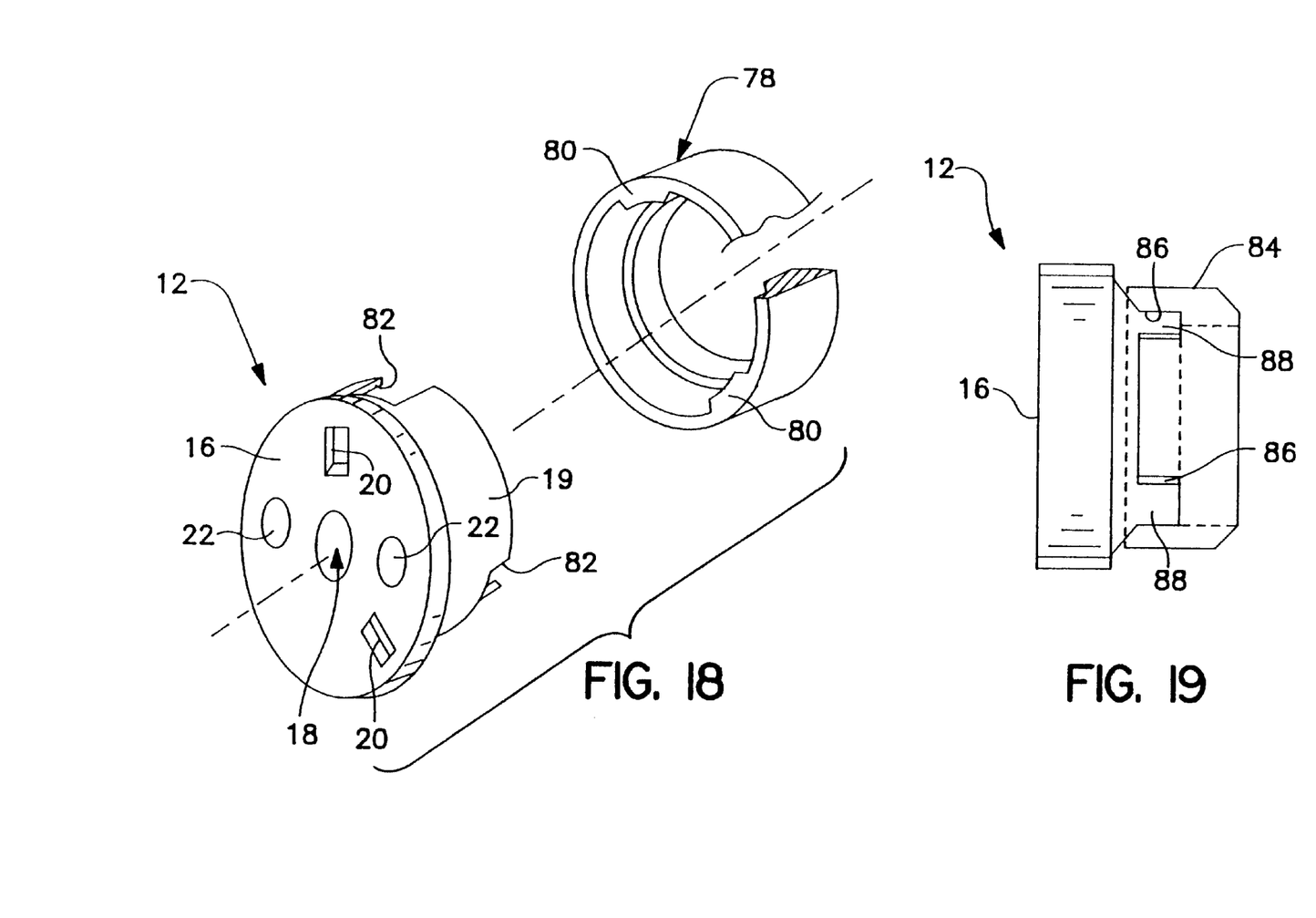
FIG. 18 is an exploded perspective view of another embodiment of the present invention.
FIG. 19 is a side elevational view of yet another embodiment of the present invention.

FIG. 18 illustrates another embodiment of the present invention which includes a molded plastic ring 78 having an inner diameter configured to slide over cylindrical surface 46 of valve body 10. Disk 78 includes radially inwardly extending key portions 80 which are aligned with machined slots 82 formed in flange 14 of cap 12.

FIG. 19 is a side elevational view illustrating another embodiment of the present invention which includes a collar 84 formed to include slots 86 configured to receive tabs 88 formed in flange 14 of cap 12. Collar 84 is configured to slide over the end of cylindrical portion 46 of valve body 10 and be glued in place to provide a key permanently coupled to valve body 10 so that only a specific keyed cap 12 can be coupled to the gas body 10.

All the sleeves are designed to be permanently installed to the valve bodies to prevent the sleeves from being removed during servicing. Therefore, the valve bodies cannot receive an inappropriate cap. The embodiments illustrated in FIGS. 7–18 do not require disassembly of the gas outlet to install the keying system. This reduces the possibility of contamination and eliminates the need to reassemble the outlet. Lower installation costs are incurred due to reduce installation time. Preferably, the caps and sleeves are color coded by gas type to facilitate matching of the appropriate cap with the appropriate sleeve and gas valve body.

Figure 20:
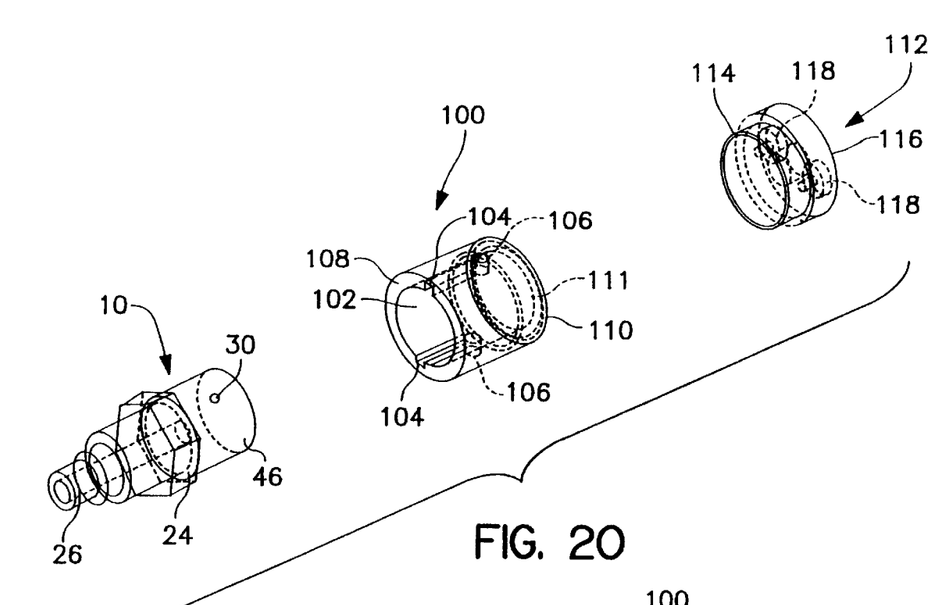
FIG. 20 is an exploded perspective view of still another embodiment of the present invention including a sleeve formed to include an annular groove, the sleeve being configured to be coupled to the valve body, and illustrating a cap having a male annular projection or ring to define a key which mates with the corresponding groove formed in the sleeve.
Figure 21:
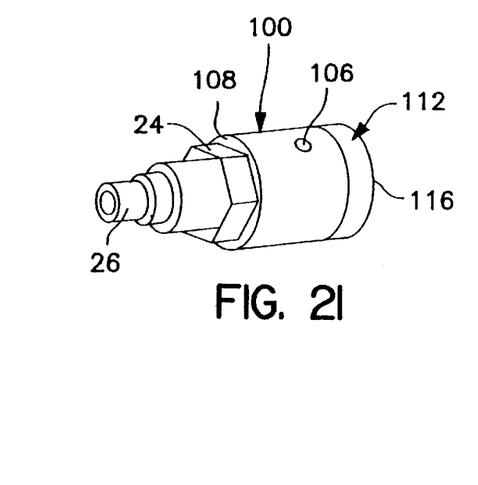
FIG. 21 is a perspective view of the components of FIG. 12 in an assembled orientation.

Another embodiment of the present invention is illustrated in FIGS. 20 and 21. In this embodiment, a sleeve 100 includes an inner wall 102 having a diameter sized to slide over cylindrical outer wall 46 of valve body 10. Sleeve 100 is permanently bonded to the cylindrical portion 46 of valve body 10 with suitable glue. Inner surface 102 is formed to include guide slots 104 on opposite sides of sleeve 100. Guide slots 104 slide over opposite set screws 30 in valve body 10. Set screws 30 therefore provide alignment with sleeve 100. Sleeve 100 is formed to include a pair of apertures 106 which are aligned with set screws 30 so that set screws 30 can be removed through the sleeve 100. Inner face 108 of sleeve 100 is configured to abut hex nut 24.

An opposite end wall 110 of sleeve 100 is formed to include an annular groove 111 having a predetermined diameter for each specific type of gas. Sleeve 100 is configured to mate with a cap 112 having an annular key or projecting ring 114 extending therefrom. Cap 112 includes a clock face 116 and is configured to receive screws 118 which are coupled to components of the valve.

The diameter of male key ring 114 is the same as the annular groove 111 so that the appropriate cap 112 mates with the appropriate sleeve 100. Different diameters of the annular groove 111 and annular ring or key 114 are provided for each specific gas. This prevents the cap 112 from being coupled to the wrong gas body 10 when sleeve 100 is secured to the valve body 10.

FIG. 21 illustrates the assembled valve body 10, sleeve 100, and cap 112. Set screws 30 are accessible through apertures 106 in sleeve 100. Set screws 30 can be removed from valve body 100 through apertures 106. The internal components of valve body 10 can then be removed by removing cap 112.

Figures 22, 23:
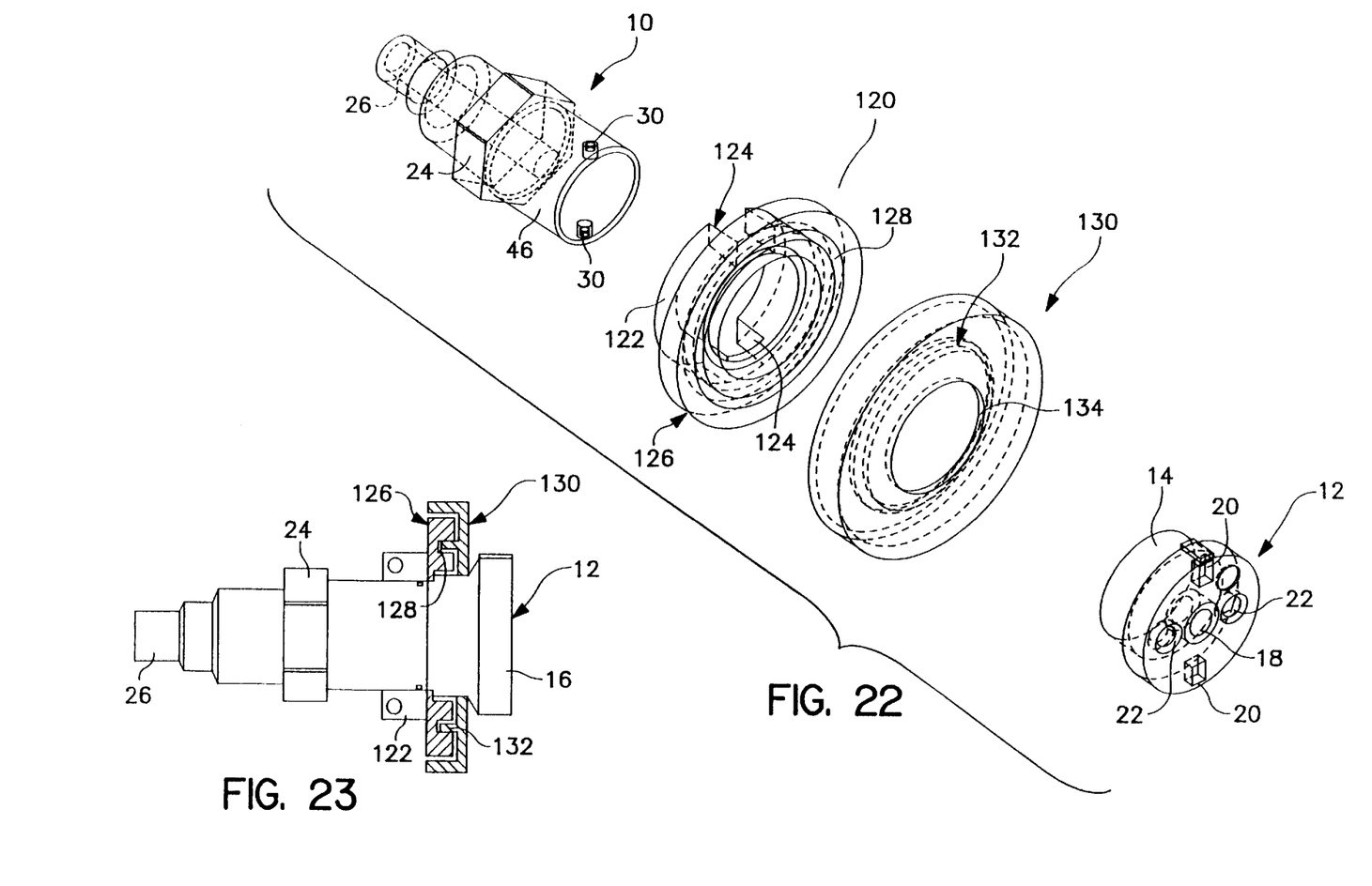
FIG. 22 is an exploded perspective view of further embodiment of the present invention.
FIG. 23 is a sectional view taken through the assembled embodiment of FIG. 22.

Another embodiment of the present invention is illustrated in FIGS. 22 and 23. In this embodiment, a collar 120 includes a flange 122 formed to include notches 124 to provide access to set screws 30 in the barrel 46 of gas outlet 10. Collar 120 includes a body portion 126 formed to include an annular groove 128 having different diameters for different gases. An outer collar 130 includes an annular inwardly projecting ring 132 configured to mate with annular groove 128 formed in body portion 126 of collar 120. Collar 130 includes a central aperture 134 configured to receive flange 14 of cap 12. Flange 14 of cap 12 is illustratively glued to the collar 130. It is understood that the collar 130 and cap 12 can be formed integrally from the same material as a single piece.

FIG. 23 illustrates the components of FIG. 22 assembled on valve body 10. The inner flange 122 is coupled to cylindrical barrel 46 of gas body 10. The annular groove 128 provides keying with the inwardly projecting ring 132 of collar 130. As discussed above, the various specific gas caps 12 are coupled to collars 130 in which the annular ring 132 has different diameters sized to mate with grooves 128. The different gases have different diameter grooves 128 and annular rings 132. Therefore, the cap 12 and collar 130 cannot be coupled to the wrong valve body 10 once the collar 120 has been installed on the valve body 10.

Figure 24:
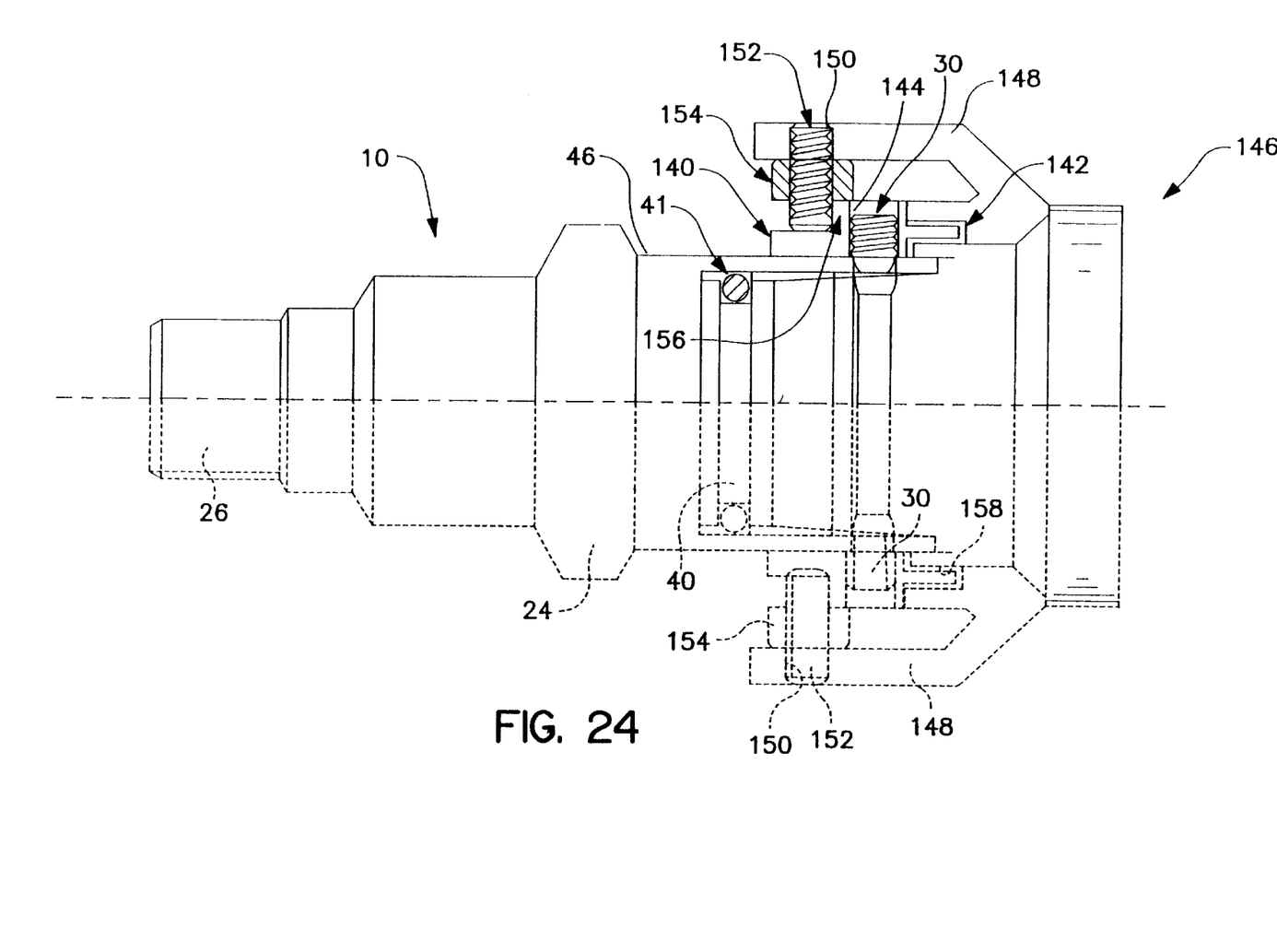
FIG. 24 is a sectional view of another embodiment of the present invention.

Another embodiment of the present invention is illustrated in FIG. 24. In this embodiment, a collar 140 includes a gas specific index ring 142 having different diameters for each gas. The collar 140 is illustratively formed of aluminum and includes threaded apertures 144 for receiving set screws 130. The collar 140 may also be glued to the cylindrical portion 46 of valve body 10. An O-ring 41 is shown on poppit valve 40.

The cap 146 includes an outer cylindrical portion 148 having apertures 150 configured to receive set screws 152. Set screws 152 extend through a metal thread ring 154 and engage a lip 156 of collar 40 to couple the cap 146 to collar 140. The cap 146 is formed to include an annular groove 158 configured to receive the ring 142 of collar 140. The ring 142 and arcuate groove 158 have matching diameters so that only the specific gas cap 146 designed to be coupled to the valve body 10 can be coupled to collar 140. There are different collars 140 and caps 146 having different diameter rings 142 and grooves 158 for each of the different specific gases.

Figure 25:
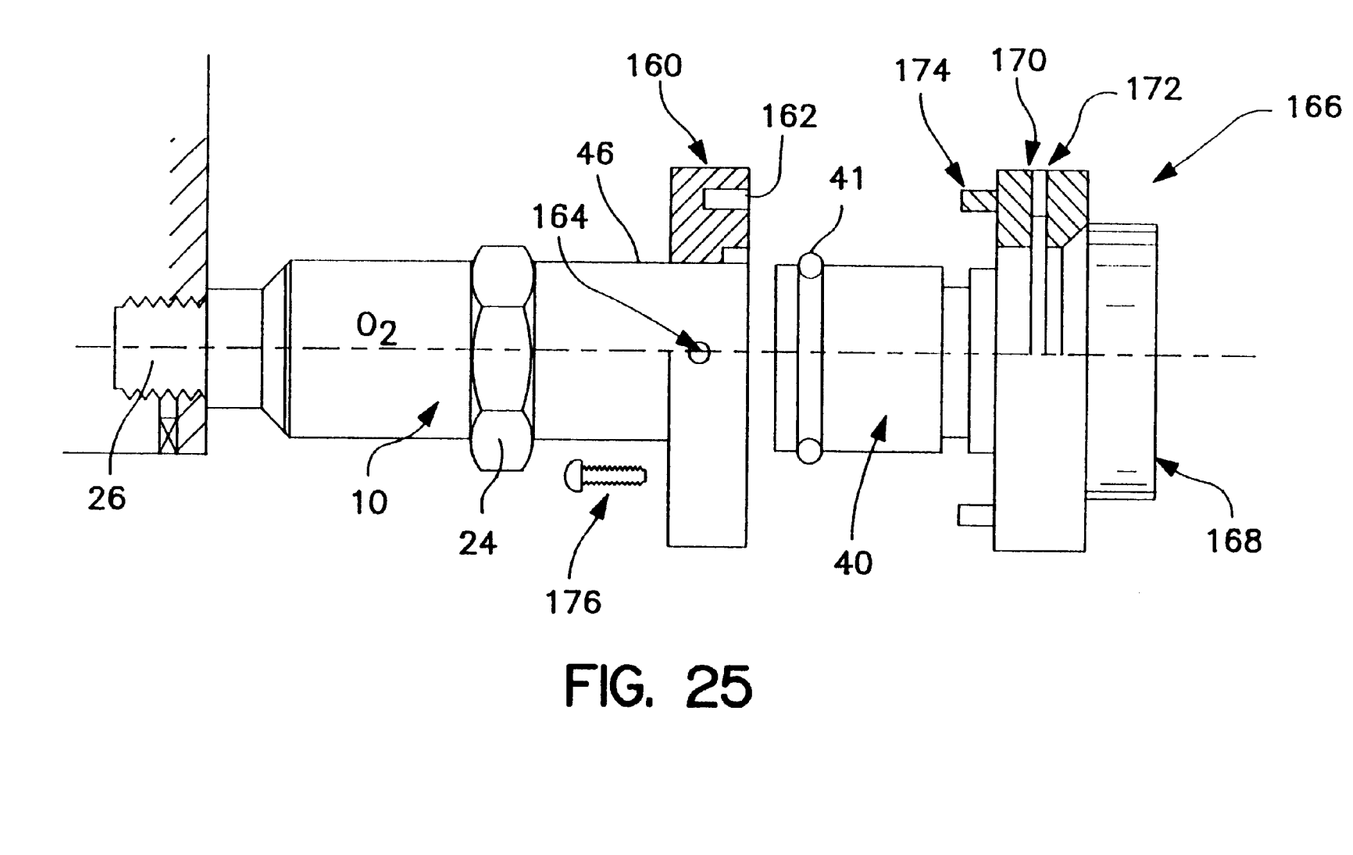
FIG. 25 is a partial sectional view of yet another embodiment of the present invention.

FIG. 25 illustrates another embodiment of the present invention which includes a gas specific collar 160 having annular groove 162 configured to be coupled to the outer cylindrical barrel 46 of gas body 10. A drive screw 164 holds collar 160 on body 10 through existing holes 36 in valve body 10. Collar 160 may also be glued to valve body 10 to permanently secure the collar 160 to valve body 10. Cap 166 includes a clock face 168 and a gas specific collar 170 having a pin and seal 172. Collar 170 includes a ring shaped projection 174 having a diameter to mate with arcuate groove 162 of collar 160. At least one fastener 176 may be used to secure the collars 160 and 170. The collars 160 and 170 are formed with different diameter grooves 162 and rings 174 to provide gas indexing or keying for gas specific caps 166.

What is claimed is:

1. A gas valve apparatus for a gas valve having a gas valve body formed to include a valve component-receiving portion open at a first end into a chamber wherein the valve components are received, said component-receiving portion having an exterior surface, configured to receive a gas specific adapter, the apparatus comprising:
    a first keying mechanism coupled to the exterior surface of the valve component-receiving portion of the gas valve body; and
    a cap coupled to the gas valve body, the cap including a keyed front face having a gas outlet configured to receive the gas specific adapter, the cap also including a second keying mechanism configured to mate with the first keying mechanism on the gas valve body to permit the cap to be coupled to the valve body.

2. The apparatus of claim 1, wherein the first keying mechanism includes a keying ring formed to include spaced apart slots, and the cap includes a flange formed to include spaced apart tabs configured to enter the spaced apart slots to permit the cap to be coupled to the gas valve body.

3. The apparatus of claim 2, wherein the keying ring is a separate ring coupled to the gas valve body.

4. The apparatus of claim 3, further comprising a set screw coupled to the gas valve body, the set screw providing a stop to position the separate ring on the gas valve body.

5. The apparatus of claim 2, wherein a separate sleeve is formed to include the spaced apart slots, the sleeve being coupled to the gas valve body.

6. The apparatus of claim 5, wherein the cap includes a collar formed to include the spaced apart tabs.

7. The apparatus of claim 2, wherein the front face of the cap includes keys spaced apart by a predetermined angle, the keys being configured to mate with keys on the gas specific adapter, the spaced apart slots formed in the ring of the first keying mechanism and the spaced apart tabs formed on the cap also being spaced apart at the predetermined angle.

8. The apparatus of claim 1, wherein the first keying mechanism is formed to include spaced apart tabs, the cap being formed to include spaced apart slots configured to receive the spaced apart tabs of the gas valve body to permit the cap to be coupled to the gas valve body.

9. The apparatus of claim 8, wherein the tabs are formed on a separate sleeve coupled to the gas valve body.

10. The apparatus of claim 1, wherein a ring is configured to be coupled to the valve body, the ring including radially inwardly extending key portions, the cap being formed to include spaced apart slots configured to receive the key portions of the ring to permit the cap to be coupled to the gas valve body.

11. The apparatus of claim 1, wherein the keying mechanism comprises a sleeve coupled to the gas valve body, the sleeve being formed to include an annular groove having a predetermined diameter, the cap including an annular flange having the same predetermined diameter as the annular groove to permit the flange to mate with the groove formed in the sleeve.

12. The apparatus of claim 11, wherein the sleeve includes an inner surface formed to include a guide slot configured to slide over a set screw coupled to the gas valve body.

13. The apparatus of claim 12, wherein the sleeve is formed to include an aperture aligned with the set screw to permit the set screw to be removed through the sleeve.

14. The apparatus of claim 1, wherein the keying mechanism comprises a sleeve a first collar coupled to the gas valve body, the first collar being formed to include an annular groove having a predetermined diameter, and a second collar coupled to the cap, the second collar being formed to include an annular ring having the same predetermined diameter as the diameter of the annular groove to permit the cap to mate with the gas valve body.

15. The apparatus of claim 1, wherein the keying mechanism comprises a collar coupled to the gas valve body, the collar being formed to include a ring having a predetermined diameter, the cap being formed to include an annular groove having a diameter the same as the predetermined diameter of the ring to permit the cap to be coupled to the gas valve body.

16. The apparatus of claim 1, wherein the gas valve body is configured to be coupled to one of a gas block, a hose in an O/R column, and a hose barb and hose suspended from a ceiling as a pendant.

17. The apparatus of claim 1, wherein the gas valve body and the gas specific adapter are each configured to supply one of oxygen, air, nitrous oxide, nitrogen, carbon dioxide, helium and vacuum.

18. A gas valve apparatus configured to receive a gas specific adapter, the apparatus comprising:
    a gas specific valve body;
    a gas specific cap coupled to the valve body, the cap including a keyed front face having a gas outlet configured to receive the gas specific adapter; and means for keying the valve body to the cap so that only the gas specific cap is capable of being coupled to the gas specific valve body.

19. The apparatus of claim 18, wherein the keying means includes spaced apart slots formed in one of the valve body and the cap, and spaced apart tabs formed on the other of the valve body and the cap, the spaced apart tabs being configured to enter the spaced apart slots to permit the cap to be coupled to the gas valve body.

20. The apparatus of claim 18, wherein the keying means includes annular groove having a predetermined diameter formed in one of the valve body and the cap, and an annular ring formed on the other of the valve body and the cap, the annular ring having the same predetermined diameter as the annular groove to permit the cap to be coupled to the valve body.

* * * * *